United States Patent [19]

Mattes et al.

[11] Patent Number: 4,666,845
[45] Date of Patent: May 19, 1987

[54] MONOCLONAL ANTIBODIES TO OVARIAN, CERVICAL AND UTERINE HUMAN CANCERS AND METHOD OF DIAGNOSIS

[75] Inventors: M. Jules Mattes, Flushing; John L. Lewis, Jr., New York; Kenneth O. Lloyd, Bronx; Lloyd J. Old, New York; Carlos Cordon-Cardo, New York, all of N.Y.

[73] Assignee: Sloan-Kettering Institute, New York, N.Y.

[21] Appl. No.: 562,465

[22] Filed: Dec. 16, 1983

[51] Int. Cl.⁴ ................ C12N 5/00; C12N 15/00; G01N 33/53; C12R 1/91
[52] U.S. Cl. .................... 435/240; 530/387; 530/808; 436/548; 436/808; 436/813; 935/96; 935/101; 935/108; 935/110; 435/68; 435/172.2; 435/241; 435/948
[58] Field of Search ............. 436/519, 520, 548, 809, 436/813, 808; 435/68, 172.2, 240, 241, 948; 935/95, 101, 96, 110, 107; 260/112 R; 530/387, 808

[56] References Cited

PUBLICATIONS

Bast, R. C. et al, *J. Clin. Invest.*, vol. 68, 1981, pp. 1331–1337.
Lloyd, K. O., in Serono Symposium No. 46, *Markers for Diagnosis and Monitoring of Human Cancer*, edited by Colnaghi, M. I. et al., 1982, pp. 205–211.
Dippold, W. G. et al., *Proc. Natl. Acad. Sci.* USA, vol. 77, No. 10, 1980, pp. 6114–6118.
Houghton, A. N. et al, *J. Exp. Med.*, vol. 156, 1982, pp. 1755–1760.
Kabawat, S. E. et al, *Amer. Soc. Clin. Path.*, vol. 79, No. 1, 1983, pp. 98–104.
Bhattacharya, M. et al, *Cancer Research*, vol. 42, 1982, pp. 1650–1654.
Old, L. J., *Cancer Research*, vol. 41, 1981, pp. 361–375.
Cordon-Cardo, C. et al, *Int. J. Gynecological Pathology*, vol. 4, 1985, pp. 121–130.

Primary Examiner—Esther M. Kepplinger
Assistant Examiner—Jeremy Jay
Attorney, Agent, or Firm—John P. White

[57] ABSTRACT

Mouse monoclonal antibodies to several cell antigens of human ovarian, cervical and endometrial carcinomas have been produced and characterized. The distribution of the antigens was determined by mixed hemagglutination assays on 153 normal and malignant cell cultures of various types, and by immunoperoxidase staining of frozen sections of 27 normal adult and 24 fetal tissues. five monoclonal antibodies representative of five classes of mAb raised to restricted ovarian, cervical and endometrial cells were tested extensively producing mAb reactive with cancer but not normal cells. One such mAb, MF116 was readily detected in the spent culture medium of metabolically radiolabeled cells. These antibodies, reacting with relatively restricted cell surface antigens, are useful in the analysis of epithelial cell differentiation, in cancer diagnosis and therapy and in tissue typing of normal or abnormal cells.

6 Claims, No Drawings

MONOCLONAL ANTIBODIES TO OVARIAN, CERVICAL AND UTERINE HUMAN CANCERS AND METHOD OF DIAGNOSIS

This invention was partially made with funds provided by the National Cancer Institute under grants CA-26184 and CA-08748. Accordingly, the U.S. Government has certain rights in this invention.

This invention relates to a method for the production of monoclonal antibodies (mAbs) to restrictive antigenic human cell components especially in human ovarian and endometrial tissues. Such mAbs have use in cancer diagnosis and therapy, as well as other cell disorders.

BACKGROUND

Conventional antisera, produced by immunizing animals with tumor cells or other antigens, contain a myriad of different antibodies differing in their specificity and properties. In 1975 Köhler and Milstein (Nature, 256:495) introduced a procedure which leads to the production of quantities of antibodies of precise and reproducible specificity. The Köhler-Milstein procedure involves the fusion of spleen cells (from an immunized animal) with an immortal myeloma cell line. By antibody testing of the fused cells (hybridomas), clones of the hybridomas are selected that produce antibody of the desired specificity. Each clone continues to produce only that one antibody, monoclonal antibody (mAb). As hybridoma cells can be cultured indefinitely (or stored frozen in liquid nitrogen), a constant, adequate supply of antibody with uniform characteristics is assured.

Antibodies are proteins that have the ability to combined with and recognize other molecules, known as antigens. Monoclonal antibodies are no different from other antibodies except that they are very uniform in their properties and recognize only one antigen or a portion of an antigen known as a determinant.

In the case of cells, the determinant recognized is an antigen on or in the cell which reacts with the antibody. It is through these cell antigens that a particular antibody recognizes, i.e. reacts with, a particular kind of cell. Thus the cell antigens are markers by which the cell is identified.

These antigenic markers may be used to observe the normal process of cell differentiation and to locate abnormalities within a given cell system. The process of differentiation is accompanied by changes in the cell surface antigenic phenotype, and antigens that distinguish cells belonging to distinct differentiation lineages or distinguish cells at different phases in the same differentiation lineage may be observed if the correct antibody is available.

The preparation of hybridoma cell lines can be successful or not depending on such experimental factors as nature of the innoculant, cell growth conditions, hybridization conditions etc. Thus it is not always possible to predict successful hybridoma preparation of one cell line although success may have been achieved with another cell line. But it is often true that selected mAb may be representative of a class of mAb raised by a particular immunogen. Members of that class share similar characteristics, reacting with the same cell antigen. Thus the invention includes hybridoma cell lines and mAb with like or similar characteristics.

Progress in defining cell surface antigens is of great importance in differentiation and disease as markers for normal and diseased cells, thereby furthering diagnosis and treatment. Thus work on melanocytes was made possible by the recently discovered technique of culturing melanocytes from normal skin (Eisinger, et al., Proc. Nat'l. Acad. Sci. U.S.A., 79 2018 (March 1982). This method provides a renewable source of proliferating cells for the analysis of melanocyte differentiation antigens. Likewise, a large number of cell lines derived from melanomas have now been established and these have facilitated the analysis of melanoma surface antigens. The advent of mAbs has greatly accelerated knowledge about the surface antigens of malignant melanoma, cell markers on both melanomas and melanocytes have been identified. A panel of typing monoclonal antibodies has been selected which recognizes differentiation antigen characteristics at each stage of development in both melanocytes and melanomas. These differentiation antigens may be used to classify melanocytes and melanomas and to group them into characteristic sub-sets. [Dippold et al. Proc. Nat'l. Acad. Sci. U.S.A. 77, 6114 (1980) and Houghton, et al, J. Exp. Med. 156, 1755 (1982)]. Immunoassay of melanocytes and melanoma cells within sub-sets is thus made possible.

Initial recognition of differentiation antigens came about through analysis of surface antigens of T-cell leukemias of the mouse and the description of the TL, Thy-1, and Lyt series of antigens. (Old, Lloyd J., Cancer Research, 41, 361–375, February 1981) The analysis of these T-cell differentiation antigens was greatly simplified by the availability of normal T cells and B cells of mouse and man. (See U.S. Pat. Nos. 4,361,549-559; 4,364,932-37 and 4,363,799 concerning mAb to Human T-cell antigens).

The existence of human leukemia specific antigens has been suggested by studies using heterologous antibodies developed by immunization with human leukemic cells [Greaves, M. F. et al. Clin. Immunol. and Immunopathol 4:67, (1975); Minowada, J., et al. J. Nat'l. Cancer Insti. 60:1269, (1978); Tanigaki, N., et al. J. Immunol. 123:2906, (1979)] or by using autologous antisera obtained from patients with leukemia [Garret, T. J., et al., Proc. Nat'l. Acad. Sci. U.S.A. 74:4587, (1977); Naito, K., et al., Proc. Nat'l. Acad. Sci. U.S.A., 80: 2341, (1983)]. The common acute lymphoblastic leukemia antigen (CALLA) which is present on leukemia cells from many patients with non-T, non-B, acute lymphoblastic leukemia (N-ALL), some chronic myelocytic leukemias (CML) in blast crisis and a few acute T-lymphoblastic leukemias (T-ALL) was originally described using conventional rabbit heteroantisera [Greaves, M. F. et al. Supra ].

By the autologous typing technique [Garret, T. J., et al. Supra; Naito, K., et al. Supra 1983; Old, L. J. Cancer Res. 41:361, (1981)], antibodies uniquely reacting with ALL cells were found in sera obtained from patients with ALL, and seemed to recognize very similar antigens to CALLA (Garret, T. J., et al. Supra; Naito, K., et al. Supra). Another leukemia associated antigen detected by heterologous antisera is the human thymus leukemia (TL)-like antigen, which is present on thymocytes as well as leukemia cells (Tanigaki, N. et al. Supra). This antigen, is therefore, a normal differentiation antigen which is composed of a heavy chain (MW 44,000–49,000) and light chain (MW 12,000–14,000) similar to the class I HLA antigens (Tanigaki, N., et al.

Supra). These investigations have, however, been hampered by the need for vigorous absorptions with normal tissues as well as the relatively small quantity and low titer of the antisera.

In vitro production of monoclonal antibodies by the technique of Köhler and Milstein, Supra has provided a better system for the identification and detection of leukemia specific antigens. A panel of monoclonal antibodies detecting cell surface antigens of human peripheral blood lymphocytes and their precursor cells have been investigated in detail [Reinherz, E. L., et al. Proc. Nat'l. Acad. Sci. U.S.A. 77:1588, (1980)]. While monoclonal antibodies detecting antigens characteristic for different lymphocyte lineages can be used for classification of human lymphocytic leukemia [Schroff, R. W., et al. Blood 59:207, (1982)], such antibodies have only limited therapeutic applications. Monoclonal antibodies detecting human leukemia associated antigens have also been produced. These include several antibodies detecting the human equivalents of the murine TL antigens. One TL-like antigen is recognized by NA134 [McMichael, A. J., et al. Eur. J. Immunol. 9:205, (1979)], OKT6 (Reinherz, E. L., et al. Supra) and Leu 6 (R. Evans, personal communication). A second TL-like antigen is recognized by M241 (Knowles, R. W., et al. Eur. J. Immunol. 12:676, 1982). Monoclonal antibodies with specificities for common acute lymphoblastic leukemia antigens J-5 (Ritz, J., et al. Nature 283:583, 1980), NL-1 and NL-22 (Ueda, R., et al. Proc. Nat'l. Acad. Sci. U.S.A. 79:4386, 1982) have also been produced. Recently, Deng, C-T, et al. Lancet. i:10, 1982) reported a complement fixing monoclonal antibody (CALLA-2) which reacts with most cultured human T-ALL cell lines and also reacts with most fresh T-ALL cells.

Mouse monoclonal antibodies to human tumor cell surface antigens have been produced in many laboratories (Lloyd, K. O. (1983) In: Basic and Clinical Tumor Immunology, Vol. 1 (R. B. Herberman, Ed.), Nijhoff, The Hague (in press)). The intention of these studies often has been to identify tumor-associated antigens that could be useful in tumor therapy or diagnosis. An inherent difficulty in this approach is the diversity of antigens on the cell surface. Although it has been possible to identify some antigens with a very restricted distribution, antibodies to antigens that elicit very weak immune responses may be missed due to their scarcity. These restricted antigens may be quite difficult to identify. Also, immunization with a complex mixture of antigens such as tumor cells may suppress the antibody response to relatively less immunogenic molecules, in a manner resembling antigenic competition (Taussig, M. J. (1973). Curr. Top. Micro. Immuno. 60:125). Thus production of mAb to restricted cell sites is an especially difficult task. The present invention provide cancer diagnosis and therapy and overcome problems heretofor encountered in the prior art with respect to ovarian and endometrial human cell antigens.

A number of ovarian tumor antigens have been detected using xenogeneic polyclonal sera (reviewed in Lloyd, K. O. (1982) Serono Symposium No. 46 (M. I. Colnagki, G. L. Buraggi and M. Ghrone, Eds.) Academic press. N.Y. pp. 205-211) but none are related to the antigens of the invention. Other laboratories have also described monoclonal antibodies to human ovarian carcinoma different from those of the invention. Bhattacharya et al. (Bhattacharya, M., et al. (1982) Cancer Res., 42:1650-1654) produced an antibody to a saline-extracted antigen detected only in mucinous cyst adenocarcinomas of the ovary and in fetal intestine. Serous cyst adenocarcinomas, the most common ovarian carcinoma, did not contain this antigen. Bast et al. produced an antibody (OC 125) reactive with an antigen present on 6/6 ovarian carcinoma cell lines and one melanoma of 14 non-ovarian cell lines tested. This antibody reacted with sections of 12/20 ovarian carcinomas and was nonreactive with 12 non-ovarian carcinomas and with most normal tissues, including normal adult and fetal ovary. Weak reactivity was observed with adult fallopian tube, endometrium and endocervix (Bast, R. C., et al. (1981) J. Clin. Invest. 68:1331-1336; Kabawat S. E., et al (1983) Amer. J. Clin. Pathol., 79:98-104).

SUMMARY

Monoclonal antibody representative of five separate classes of mAb to ovarian and uterine cancers are described. The antigenic profile of each of these mAbs is presented with both serological and tissue reactivity studies in cancer and normal cell lines and tissue sections. These mAbs form a panel useful for the diagnosis and therapy of cancers of the ovarian and uterine system.

DESCRIPTION

The techniques described below result in the isolation of mAb of several classes; representative mAbs from each of these classes are described and characterized. These techniques can be used to isolate other mAbs from these classes. Thus substantially similar or functionally equivalent monoclonal antibodies having substantially the same characteristics and properties can be produced in accordance with the procedures of the invention. The mAb examples described herein are for illustrative purposes only and are not meant to limit the invention in any way.

Target cells

Cell lines used are listed in Table I. Preparation of cultures of normal human fibroblasts, kidney epithelial cells and melanocytes have been described (Carey, T. E., et al. (1976) Proc. Nat'l. Acad. Sci., U.S.A., 73:3278-3282; Ueda, R., et al. (1979). J. Exp. Med., 150:564-579; Eisinger, M., et al. (1982) Proc. Nat'l. Acad. Sci., U.S.A., 79:2018-2022). Adherent cells were maintained in Eagle's minimum essential medium (GIBCO, Grand Island, NY) supplemented with 2.5% fetal calf serum, 5% newborn calf serum, 100 U/ml penicillin and 1 mg/ml streptomycin. Nonadherent cells were cultured in RPMI 1640 medium supplemented similarly except with 7.5% fetal calf serum. Cultures were regularly tested for mycoplasma and contaminated cultures discarded.

Normal blood mononuclear cells were obtained by centrifuging heparinized blood onto a layer of Ficoll-Paque (Pharmacia, Piscataway, NJ). Total blood leukocytes were obtained by collecting the buffy coat after centrifugation for 10 min at 600 g in 100 microliter capillary tubes.

The origins of cells and tissues is as follows: Drs. Charles Welander, Sloan-Kettering Institute, New York, N.Y. (SK-OV-6 and SK-UT-1), Jorgen Fogh, Sloan-Kettering Institute, New York, N.Y. (SK-OV-3 and SW626), G. Roos, University of Umea at Umea, Sweden (A7 and A10), George Moore, Denver General Hospital, Denver, Colo. (COLO 316) and R. S. Freedman University of Texas, at Houston (2774), Dr. Virginia Pierce for clinical specimens, the Human Cancer Serology group for cell lines and tissue specimens.

Production of Mouse Monoclonal Antibodies

BALB/c or (BALB/c×C57BL/6)F$_1$ mice were immunized with the ovarian carcinoma cell lines SK-OV-3, SW626 or 2774, or the endometrial carcinoma cell line SK-UT-1. Intraperitoneal injections of approximately 100 microliters of packed cells were given 2-5 times at intervals of two weeks. Three days after the last injection, the fusion of immune spleen cells with mouse myeloma MOPC-21 NS/1 cells was performed as described (Dippold, W. G., (1980) Proc. Nat'l. Acad. Sci., U.S.A., 77:6114-6118). Initially, cells were plated in 480 wells (Costar 3524, 24 well plates) Hybridoma cultures were subcloned at least two times by limiting dilution in 96 well plates on a feeder layer of normal mouse spleen cells. Culture supernatants were monitored for antibody activity by the anti-mouse Ig MHA (mixed hemagglutination assay) method on a panel of cultured cells consisting of the immunizing cell line and other types of human tumor cells. Cloned hybridoma cells were injected subcutaneously into nu/nu mice. Sera from mice with progressively growing tumors were collected and used for serological and biochemical characterization. Antibody subclass was determined by double diffusion in agar with anti-Ig heavy chain-specific reagents (Bionetics, Kensington, MD).

Serological Procedures

For adherent target cells, 200-500 trypsinized cells were plated in 10 microliters in wells of Terasaki plates (Falcon microtest plates 3034) and allowed to adhere overnight. Nonadherent target cells were attached to the wells by pretreating the wells with concanavalin A (con A, grade IV, Sigma Chemicals, St. Louis, MO) (Mattes, M. J., et al. (1983) J. Immunol. Metho., 61:145-150). The mixed hemagglutination (MHA) assay, using rabbit anti-mouse Ig, has been described (Ueda, R., et al. (1979) J. Exp. Med., 150:564-579). The CrCl$_3$ conjugation procedure has been described (Koo, G. C., et al. (1978) J. Immunol. Meth., 23:197-201), except that undiluted rabbit anti-mouse IgG (DAKO, Accurate Chemicals, Westbury, NY) or the IgG fraction of goat anti-mouse IgM (Cappel Laboratories, Cochranville, PA), at 4.0 mg/ml, was used instead of Protein A. Monoclonal sera were titrated starting at $10^{-3}$. To confirm the specificity of antibodies, absorption tests were performed with the immunizing cell line and three melanomas (SK-MEL-28, SK-MEL-37 and MeWo), three astrocytomas (SK-MG-1, SK-MG-3 and U373 MG), three carcinomas (SK-BR-3, SK-LC-6 and Scaber), one T cell leukemia (MOLT-4), one B cell leukemia (Raji) and human erythrocytes. Absorption procedures have been described (Carey, T. E., et al. (1976) Supra.

To test heat stability of antigens, cells were heated 5 min. at 100° C. before performing absorption tests. To test the hydrophobic nature of antigens, cell pellets were extracted with 20 volumes of chloroform methanol, 2:1. Solubilized material was dried and resuspended with sonication in Dulbecco's phosphate-buffered saline (GIBCO), 0.5% bovine albumin (fraction V, Sigma Chemicals), to a volume equal to the original packed cell volume. This suspension was assayed for inhibitory activity of the appropriate antibody.

Immunoperoxidase staining of sections employed 5 micrometer cryostat sections. Air-dried sections were fixed for 10 min at room temperature with 2.0% buffered formaldehyde (Farr, A. G., et al. (1981) J. Immunol. Meth., 47:129-144). A triple sandwich was used routinely which consisted of monoclonal antibody (nu/nu mouse serum at 1/500), biotinylated horse anti-mouse Ig, and complexes of avidin and biotinylated horseradish peroxidase (Vectastain reagents, Vector Laboratories, Burlingame, CA), following procedures recommended by the manufacturer. For particular tissues that had excessive background with this procedure, namely the kidney, liver and pancreas, a double sandwich was used which comprised monoclonal sera at 1/200 and peroxidase-conjugated anti-mouse Ig (DAKO P161) at 1/50. To ensure that fixation did not destroy the antigen investigated, each antibody was first tested on sections of tissue culture cells frozen in 10% dimethylsulfoxide at 50% (packed cell volume/volume). All antibodies tested were positive in this assay, when the immunizing cell line was used as the target.

Immunofluorescent staining of blood leukocytes in suspension was performed as described (Mattes, M. J., et al. (1979) J. Immunol., 123: 2851-2860) using fluorescein-conjugated goat anti-mouse Ig (Cappel Laboratories) at 1/40, and monoclonal sera at 1/50. Lymphocytes and granulocytes were distinguished by morphology.

Immunoprecipitation Procedures

Each antibody was tested for its ability to precipitate an antigen from detergent-solubilized extracts of the immunizing cell after labeling by three methods: metabolic incorporation of [$^3$H] glucosamine (Ogata, S-I, et al. (1981) Proc. Nat'l. Acad. Sci., U.S.A. 78:770-774), metabolic incorporation of [$^{35}$S]methionine (Dippold, W. G., et al. (1980) Proc. Nat'l. Acad. Sci., U.S.A., 77:6114-6118), or chloramine T $^{125}$I labeling of solubilized cell membranes (Cairncross, J. G., et al, (1982) Proc. Nat'l. Acad. Sci., U.S.A., 79:5641-5645). NP40 solubilization of labeled cells and con A-Sepharose fractionation of labeled extracts, used in some experiments, have been described (Dippold, W. G., et al. (1980), Supra; Ogata, S-I, et al, (1981), Supra, Cairncross, J. G., et al. (1982), Supra), as have immunoprecipitation procedures for $^{125}$I-labeled samples, using Staphylococcus aureus (Cairncross, J. G., et al. Supra (1982)).

Aliquots of $2 \times 10^6$ [$^{35}$S] cpm from unfractionated cell extracts were handled similarly except that preclearing was omitted. For the con A eluate fraction of [$^{35}$S]-labeled extracts and for [$^3$H]-labeled extracts, aliquots of $2 \times 10^5$ cpm and different washing buffers (Lloyd, K. O., et al. (1981) J. Immunol., 126:2408-2413) were used. Precipitated molecules were extracted with 60 microliter 0.01 M Tris HCl pH 7.2, 2.0% NaDodSO$_4$ (sodium dodecylsulfate), 12.0 mg/ml dithiothreitol (DTT), 15% (wt/vol) sucrose, 0.01% pyronin Y by heating 5 min at 100° C., and analyzed by polyacrylamide gel electrophoresis (PAGE) (Dippold, W. G., et al. (1980) Supra; Laemmli, U. K., (1970) Nature 227:680-685), using 9% gels. For 2-dimensional electrophoresis (isoelectric focusing followed by NaDodSO$_4$-electrophoresis), immune precipitates were extracted and handled as described (Ogata, S-I, et al. (1981) Supra; O'Farrell, P. H., et al. in Method in Cell Biology (Prescott, D. M., Eds.) (1977) Academic Press, New York, Vol. 16, pp. 407-420)). For unreduced samples, DTT was omitted and 14.0 mg/ml iodacetamide was added to samples.

Selection of Hybridomas

Monoclonal antibodies (mAb) MD144, MF61, MF116, ME195 and ME46 were obtained after immunization with ovarian carcinoma cell line 2774, and mAbs MH55 and MH94 were obtained after immunization with endometrial carcinoma cell line SK-UT-1. The heavy chain subclasses of the seven antibodies are: MD144, gamma-sub one; MH55, mu; MF61, mu; MF116, gamma-sub two A; ME46, gamma-sub one; ME195, gamma-sub one; MH94, gamma-sub one. These monoclonal antibodies were initially selected for cloning on the basis of reactivity with the immunizing cell line and lack of reactivity with three melanomas and three astrocytomas. These antibodies were produced from a total of 12 fusions from mice immunized with human ovarian and uterine cancer cell lines. A total of 430 of the supernatants contained antibodies reacting with the immunizing line. Twelve cultures were selected for subcloning, and ten hybridomas were propagated successfully. The properties of seven antibodies are discussed in this publication and two other antibodies, which detected more wide-spread antigens, are described elsewhere (Mattes, M. J., et al. *Hybridoma* (1983) 2:523. None of these mAbs reacted with glycoproteins carrying A, B, H, Le$^a$, Le$^b$, X, Y or I blood group structures.

TABLE I

Reactivity of mouse monoclonal antibodies with cultured human cells and cell lines

| CELLS | mAb MD144 | | | | mAb MF61 | | | | mAb MF116 | | | | mAb MH94 | | | |
|---|---|---|---|---|---|---|---|---|---|---|---|---|---|---|---|---|
| Ovarian carcinomas | | | | | | | | | | | | | | | | |
| 2774, SK-OV-6, SW 626, SK-OV-3 | 2 | 0 | 0 | 0[1] | 2 | 0 | 0 | 0 | 2 | 0 | 0 | 0 | 0 | 2 | 2 | 0 |
| SK-OV-4, Colo 316, A7, A10 | 0 | 0 | 0 | 0 | 0 | 0 | 0 | 0 | 0 | 0 | 0 | 0 | 0 | 0 | 0 | 0 |
| SW 626 | 0 | | | | 0 | | | | 0 | | | | 0 | | | |
| Endometrial carcinoma | | | | | | | | | | | | | | | | |
| SK-UT-1 | 0 | | | | 0 | | | | 2 | | | | 2 | | | |
| Renal carcinoma | | | | | | | | | | | | | | | | |
| SK-RC-1, -2, -7, -8 | 0 | 0 | 0 | 0 | 2 | 0 | 0 | 0 | 2 | 2 | 2 | 2 | 0 | 0 | 0 | 0 |
| SK-RC-9, -10, -12, -17 | 0 | | 0 | 0 | 0 | 2 | 2 | 2 | 2 | | 2 | 0 | 0 | | 0 | 0 |
| SK-RC-35, Caki-2, SK-RC-4, -6 | 0 | 0 | 0 | 0 | 2 | 2 | 0 | 0 | 0 | 0 | 0 | 0 | 0 | 0 | 0 | 0 |
| SK-RC-16, -28, Caki-1 | 0 | 0 | 0 | | 0 | 0 | 0 | | 0 | 0 | 0 | | 0 | 0 | 0 | |
| Bladder carcinomas | | | | | | | | | | | | | | | | |
| 253J, SCABER, RT4, VM-CUB-1 | 0 | 0 | 0 | 0 | 0 | 0 | 0 | 0 | 2 | 0 | 0 | 0 | 0 | 0 | 0 | 0 |
| VM-CUB-2, 5637, 639-V, J82 | 0 | 0 | 0 | 0 | 0 | 0 | 0 | 0 | 0 | 0 | 0 | 0 | 0 | 0 | 0 | 0 |
| 486-P, JCCSUP | 0 | 0 | | | 0 | 0 | | | 0 | 0 | | | 0 | 0 | | |
| Colon carcinomas | | | | | | | | | | | | | | | | |
| SK-CO-10, SW403, SW480, SK-CO-1 | 0 | 0 | 0 | 0 | 0 | 0 | 0 | 0 | 0 | 0 | 0 | 0 | 2 | 2 | 1 | 0 |
| SW620, SW1222, HT-29 | 0 | 0 | 0 | | 0 | 0 | 0 | | 0 | 0 | 0 | | 0 | 0 | 0 | |
| Breast carcinomas | | | | | | | | | | | | | | | | |
| CAMA, SK-BR-3, -5, BT-20 | 0 | 0 | 0 | 0 | 0 | 0 | 0 | 0 | 0 | 0 | 0 | 0 | 2 | 0 | 0 | 0 |
| BT-474, MCF-7, AlAb, ZR-75-1 | 0 | 0 | 0 | 0 | 0 | 0 | 0 | 0 | 0 | 0 | 0 | 0 | 0 | 0 | 0 | 0 |
| DA-MB-361, MDA-MG-231 | 0 | 0 | | | 0 | 0 | | | 0 | 0 | | | 0 | 0 | | |
| Lung carcinomas | | | | | | | | | | | | | | | | |
| SK-LC-9, -15, -1, -2 | 0 | 0 | 0 | 0 | 0 | 0 | 0 | 0 | 0 | 0 | 0 | 0 | 2 | 2 | 0 | 0 |
| SK-LC-3, -4, -5, -6 | 0 | 0 | 0 | 0 | 0 | 0 | 0 | 0 | 0 | 0 | 0 | 0 | 0 | 0 | 0 | 0 |
| SK-LC-7, -8, -10, -13 | 0 | 0 | 0 | 0 | 0 | 0 | 0 | 0 | 0 | 0 | 0 | 0 | 0 | 0 | 0 | 0 |
| SK-LC-14, -16, Calu-1, SK-LC-LL | 0 | 0 | 0 | 0 | 0 | 0 | 0 | 0 | 0 | 0 | 0 | 0 | 0 | 0 | 0 | 0 |
| SL-LC-12 | 0 | | | | 0 | | | | 0 | | | | 0 | | | |
| Cervical carcinoma | | | | | | | | | | | | | | | | |
| ME 180 | 0 | | | | 0 | | | | 0 | | | | 1 | | | |
| Pancreatic carcinomas | | | | | | | | | | | | | | | | |
| CAPAN-1, -2, ASPC-1 | 0 | 0 | 0 | | 0 | 0 | 0 | | 0 | 0 | 0 | | 0 | 2 | 0 | |
| Neuroblastomas | | | | | | | | | | | | | | | | |
| LA-N-15, SK-N-sSH, -MC, LA-N-Is | 0 | 0 | 0 | 0 | 0 | 0 | 0 | 0 | 2 | 0 | 0 | 0 | 0 | 0 | 0 | 0 |
| SH-EP1, SK-N-BE(2) | 0 | 0 | | | 0 | 0 | | | 0 | 0 | | | 0 | 0 | | |
| Melanomas | | | | | | | | | | | | | | | | |
| SK-MEL-13, -19, -23, -26 | 0 | 0 | 0 | 0 | 0 | 0 | 0 | | 0 | 0 | 0 | | 0 | 0 | 0 | |
| SK-MEL-28, -29, -31, -37 | 0 | 0 | 0 | 0 | 0 | 0 | 0 | 0 | 0 | 0 | 0 | 0 | 0 | 0 | 0 | 0 |
| SK-MEL-75, -93-2, -93-3, -127 | 0 | 0 | 0 | 0 | 0 | 0 | 0 | 0 | 0 | 0 | 0 | 0 | 0 | 0 | 0 | 0 |
| SK-MEL-130, -153, MeWo | 0 | 0 | 0 | | 0 | 0 | 0 | | 0 | 0 | 0 | | 0 | 0 | 0 | |
| Astrocytomas | | | | | | | | | | | | | | | | |
| SK-MG-1, -2, -3, -5 | 0 | 0 | 0 | 0 | 0 | 0 | 0 | 0 | 0 | 0 | 0 | 0 | 0 | 0 | 0 | 0 |
| SK-MG-6, -8, -11, -14 | 0 | 0 | 0 | 0 | 0 | 0 | 0 | 0 | 0 | 0 | 0 | 0 | 0 | 0 | 0 | 0 |
| SK-MG-15, U138MG, U251MG, U373MG | 0 | 0 | 0 | 0 | 0 | 0 | 0 | 0 | 0 | 0 | 0 | 0 | 0 | 0 | 0 | 0 |
| Other carcinomas | | | | | | | | | | | | | | | | |
| SK-HEP-1 (heptoma), G cc-SV | 0 | 0 | | | 0 | 0 | | | 0 | 0 | | | 0 | 0 | | |
| T-cell lymphomas and leukemias | | | | | | | | | | | | | | | | |
| MOLT4, CCRF-HSB-2, CCRF-CEM, 45 | 0 | 0 | 0 | 0 | 0 | 0 | 0 | 0 | 0 | 0 | 0 | 0 | 0 | 0 | 0 | 0 |
| Peer, P12/Ichikawa, HPB-ALL | 0 | 0 | 0 | | 0 | 0 | 0 | | 0 | 0 | 0 | | 0 | 0 | 0 | |
| B-cell lymphomas and leukemias | | | | | | | | | | | | | | | | |
| SK-LY-16, -18, Daudi, Ball-1 | 0 | 0 | 0 | 0 | 0 | 0 | 0 | 0 | 0 | 0 | 0 | 0 | 0 | 0 | 0 | 0 |
| SK-DLH-2, ARA-10, Raji | 0 | 0 | 0 | | 0 | 0 | 0 | | 0 | 0 | 0 | | 0 | 0 | 0 | |
| Null-cell leukemias | | | | | | | | | | | | | | | | |
| NALM-1, -16 | 0 | 0 | | | 0 | 0 | | | 0 | 0 | | | 0 | 0 | | |
| Myeloid leukemias | | | | | | | | | | | | | | | | |
| HL-60, K562, KG-1 | 0 | 0 | 0 | | 0 | 0 | 0 | | 0 | 0 | 0 | | 0 | 0 | 0 | |
| Myelomas | | | | | | | | | | | | | | | | |

TABLE I-continued

Reactivity of mouse monoclonal antibodies with cultured human cells and cell lines

| CELLS | mAb MD144 | | | mAb MF61 | | | mAb MF116 | | | mAb MH94 | | |
|---|---|---|---|---|---|---|---|---|---|---|---|---|
| SK-MY-1, LICR-Lon-HMy-2 | 0 | 0 | 0 | 0 | 0 | 0 | 0 | 0 | 0 | 0 | 0 | 0 |
| Monocytic leukemia | | | | | | | | | | | | |
| U937 | 0 | | | 0 | | | 0 | | | 0 | | |
| Normal cells | | | | | | | | | | | | |
| Fibroblasts (6), melanocytes | 0 | 0 | | 0 | 0 | | 0 | 0 | | 0 | 0 | |
| Kidney epithelia, 1, 2 | 0 | 0 | | 0 | 0 | | 2 | 1 | | 0 | 0 | |
| Non-human cells | | | | | | | | | | | | |
| Vero, CHO | 0 | 0 | | 0 | 0 | | 0 | 0 | | 0 | 0 | |

[1] The symbols listed under the antibodies refer to the titer against the cell line in the corresponding position in the left hand side of the Table. The titer of the antibody was defined as the highest dilution producing at least 50% rosetting in the MHA assay. Symbols are: 2 = a range of $1 \times 10^{-3} - 1 \times 10^{-6}$; 1 = positive reaction but with less than 50% rosetting at $10^{-3}$ dilution of antibody; 0 = no reactivity at antibody dilution of $10^{-3}$.

TABLE II

Summary of reactivities of monoclonal antibodies

| ANTIBODY | ON TISSUE CULTURE CELLS[1] | ON NORMAL ADULT TISSUE SECTIONS[2] | ON NORMAL FETAL TISSUE SECTIONS[3] |
|---|---|---|---|
| MD144 | Ovarian carcinomas (1/8) | Negative | N.T.[4] |
| MH55 | Ovarian (3/8) and uterine (1/1) carcinomas | Negative | N.T. |
| MF61 | Ovarian (1/8) and renal (6/16) carcinomas | Uterine epithelial cells and thyroid colloid positive | Uterine epithelial cells positive |
| MH94 | Ovarian (2/8), uterine (1/1), colon (3/7), breast (1/10), lung (2/18) and cervical (1/1) carcinomas | Pancreas, ureter, breast, prostate, cervix, urinary bladder epithelial cells, sweat and sebaceous glands of skin positive | Stomach, intestine, pancreas, ureter, urinary bladder, uterus and cervix epithelial cells positive |
| MF116 | Normal kidney epithelial cells; ovarian (1/8), uterine (1/1), renal (6/16), bladder (1/10), carcinomas and neuroblastomas (1/6). | Negative | Negative |

[1] Antibodies were tested on 153 cell lines of various types (Table I). All tests except those listed were negative.
[2] Antibodies were tested on sections of 27 normal adult tissues: lung, heart, liver, spleen, gall bladder, esophagus, stomach, small intestine, colon, pancreas, kidney, ureter, urinary bladder, adrenal, thyroid, breast, prostate, testes, ovary, fallopian tube, uterus, cervix, placenta, skin, brain, lymph nodes and muscle. Tissues not listed were negative.
[3] Antibodies were tested on 24 normal fetal tissues: lung, heart, spleen, thymus, liver, gall bladder, esophagus, stomach, small intestine, colon, pancreas, kidney, ureter, urinary bladder, adrenal, testes, ovary, fallopian tube, uterus, cervix, skin, brain lymph nodes and muscle. Tissues not listed were negative.
[4] N.T.: not tested.

MD144

Ab MD144 reacted with only a single ovarian carcinoma cell line, 2774, with a titer of $10^4$ by immune rosetting; all 152 other cell lines tested were negative (Table I). The antigen was not detected in sections of the normal tissues (Table II). Absorption experiments also did not detect the antigen on any cell type except 2774; in this assay, 1-3 microliters of packed cells was required for nearly complete absorption. The antigen was not destroyed by heating at 100° C. for 5 min, and it was present in the chloroform:methanol extract of 2774 cells. In immunoprecipitation experiments using cell extracts labeled with [$^3$H]glucosamine but not with [$^{35}$S]methionine, counts were precipitated which migrated at the dye front in both 9% and 12.5% acrylamide gels. These properties all strongly suggest that the antigen is a lipid.

MH55

Ab MH55 is an IgM antibody which reacts weakly with 4/8 ovarian carcinomas (2774, SK-OV-6, A10 and A7) and 1/1 uterine carcinoma (SK-UT-1) with a titer of $10^{-3}$ or lower; all 148 other cell types tested were negative. Varying the temperature of incubation with antibody, the density of the target cells, and the time interval between target cell plating and testing did not improve the titer or the consistency. We therefore have not done absorption experiments. Ab MH55 did not react with any tissue sections examined but it did react with sections of frozen pellets of A10 ovarian carcinoma cells.

MF61

Antibody MF61 reacted with ⅛ ovarian carcinoma and 6/16 renal carcinoma cell lines (Table I); the other 146 cell types tested were negative. Absorption experiments revealed no additional positive cell types. Blood leukocytes were negative by immunofluorescence. Absorption tests were unusually sensitive, in that 0.1 microliters of packed cells absorbed nearly completely; negative absorption under our standard conditions therefore indicates at least a 300-fold lower expression of antigen than on the immunizing cell line. MF61 antigen, like the MD144 antigen, was heat-stable and soluble in chloroform:methanol. The chloroform:methanol extracts were as active as intact cells in absorption experiments. Also, antibody MF61 immunoprecipitated counts from [$^3$H]glucosamine-labeled cell extracts that migrated at the dye front in both 9% and 12.5% acrylamide gels (FIG. 1). It is believed that this antigen is a lipid.

In tissue sections, antibody MF61 reacted with two normal tissues: glandular epithelial cells of the adult and fetal uterus and the noncellular follicles of the thyroid. It also reacted with the follicles of a pig thyroid.

MF116

Three antibodies were obtained from two fusions which react with the same antigen, of which the prototype antibody is MF116. The other two antibodies, ME46 and ME195, are IgG$_1$, while antibody MF116 is IgG$_{2a}$. Antibody MF116 reacted with ⅛ ovarian carcinoma, 1/1 endometrial carcinoma, 6/16 renal carcinoma, 1/10 bladder carcinoma and 1/6 neuroblastoma cell lines. It also reacted with 2/2 normal kidney epithelial cell cultures (Table I). The other 141 cell types tested were negative. Absorption experiments revealed no additional positive cells; 10 microliters of packed cells was required for nearly complete absorption; this result is consistent with a low expression of antigen on the cell surface. Blood leukocytes were negative by immunofluorescence. By immunoperoxidase, MF116 was not detected in any normal tissues examined, including normal kidney, ovary and uterus.

MF116 antigen was immunoprecipitated from [$^3$H]glucosamine or [$^{35}$S]methionine labeled spent medium from ovarian carcinoma 2774. No antigen was detected in solubilized cell extracts labeled with [$^3$H]glucosamine, [$^{35}$S]methionine or $^{125}$I. This antigen is preferentially shed or secreted in the medium, although it must be present on the cell surface since it is detected in rosetting assays. The molecular weight is 105,000, as estimated by PAGE. If the antigen was not reduced, it migrated slightly faster, indicating some intrachain disulfide bonds. The isoelectric point was determined to be less than pH 4.0, since the antigen migrated at or off the acidic end of the isoelectric focusing gel. This antigen bound to concanavalin A-Sepharose and was eluted with methyl-alpha-D-mannoside. The antigen was destroyed by heating at 100° C., as determined in absorption experiments. MF116 was not detected by immunoprecipitation in the spent medium of two other cell lines (SK-UT-1 and SK-RC-1) that were positive by rosetting.

MH94

MH94 antigen was detected on various carcinoma cell lines, being detected on 2/8 ovarian carcinoma, 1/1 endometrial carcinoma, 3/7 colon carcinoma, 1/10 breast carcinoma, 2/18 lung carcinoma, 1/1 cervical carcinoma and 1/3 pancreatic carcinoma cell lines (Table I). All 142 other cell types tested were negative. Absorption experiments did not reveal additional positive cells; 3 microliters packed SK-UT-1 cells gave nearly complete absorption. Blood leukocytes were negative by immunofluorescence. By immunoperoxidase, MH94 was detected in the acinar and duct lining cells of the pancreas, the epithelial cells of the ureter, breast, pancreas, cervix and urinary bladder and the sweat and sebaceous glands of the skin. It was also found in fetal stomach, intestine, pancreas, ureter, urinary bladder, endometrium and endocervix.

The MH94 antigen was not destroyed by heating to 100° C., but was not detected in a chloroform:methanol extract of cells. It was not precipitated under any conditions tested, which included labeling two cell lines with three isotopes.

These studies describe five specific mAbs detecting highly restricted antigens that are of considerable interest for the analysis of ovarian and uterine tumors (Table II). More broadly reactive antibodies derived from the same fusions, recognizing glycoprotein antigens, were described previously (Mattes, M. J., et al. *Hybridoma* (1983) 2:523. These antibodies generally had higher titers than the ones described here, perhaps reflecting the characteristics of the antigens recognized as discussed below.

Both MD144 and MF61 antigens have properties of lipids or hydrophobic proteins. A substantial fraction of very restricted mouse monoclonal antibodies, produced in several laboratories, have recognized glycolipids (Pukel, C. S., et al. (1982) J. Exp. Med., 155:1133-1147; Nudelman, E., et al. (1982) J. Biol. Chem., 257:12752-12756; Magnani, J. L., et al. (1981) Science, 212:55-56), a result which was quite unexpected on the basis of previous work using whole xenoantisera to human tumor cells. Resistance to heating at 100° C., which is one of their characteristics, could be a property of lipids, carbohydrate determinants on glycoproteins or of exceptional protein determinants. MD144 and MF61 antigens are soluble in chloroform methanol, but this does not distinguish between lipids and hydrophobic proteins (Audubert, F., et al. (1979) Biochem. Biophys. Res. Comm., 91:416-426). Likewise, the immunoprecipitation by mAbs MD144 and MF61 of counts running at the dye front in acrylamide gel electrophoresis, after labeling with [$^3$H]glucosamine, is true of glycolipids as well as small glycoproteins, which would have similar properties. Also, we have evidence that some hydrophobic interactions are not completely disrupted in the presence of the detergents used to solubilize cells, so glycolipids might be co-precipitated by antibodies to hydrophobic proteins or to a nonglycosylated lipid.

MD144 antigen which is found only a single ovarian cancer cell line, is unique. This component is believed to be: a rare human allele, or a rarely expressed gene product, or a mutant form of a normal cell component. Although unique antigens have been demonstrated on chemically induced animal tumors (Baldwin, R. W. (1973) Adv. Cancer Res., 18:1-75) and on human tumors (Old, L. J. (1981) Cancer Res., 41:361-375), present data indicate that these antigens are proteins or glycoproteins (DuBois, G. C., et al. (1982) Proc. Nat'l. Acad. Sci., U.S.A. 79:7669-7673; Carey, T. E., et al. (1979) Proc. Nat'l. Acad. Sci., U.S.A. 76:2898-2902; Real, F. X., et al. (1983) Proc. Amer. Assoc. Cancer Res., 24:233) and therefore differ in this respect from MD144. MF61 has an unusual distribution in normal tissue, being present in the noncellular follicles of the thyroid and in uterine glandular epithelial cells. The dominant antigen of the thyroid colloid is thyroglobulin, but antibody MF61 was not reactive with human thyroglobulin. A second colloid antigen has been described (Balfour, B. M., et al. (1961) Brit. J. Exp. Pathol, 42:307-316), but has not been characterized biochemically. On tumor cells, MF61 is very restricted in its distribution, being detected only one ovarian carcinoma line and six renal carcinoma cell lines.

MH94 was detected on a small fraction of carcinoma cell lines tested, including carcinomas of the ovary, uterus, colon, breast, lung, cervix and pancreas. The fact that this antigen was detected on only 1/10 breast carcinomas and 2/20 lung carcinomas indicates the importance of testing many cell lines of each tumor type in determining the distribution of an antigen. In frozen sections, MH94 was detected in secretory epithelial cells of many normal tissues.

On tissue culture cells, MF116 was found on normal kidney cells as well as on some carcinomas of the ovary, uterus, kidney, bladder and on one neuroblastoma. The most frequent tumor type that was positive was renal carcinoma, for which 6/16 cell lines were positive. MF116 was not detected in sections of any normal tissue. The presence of MF116 on normal kidney cells in tissue culture and its absence from frozen sections of normal kidney cannot presently be explained, but might suggest that antigen expression is increased in rapidly proliferating cells. MF116 is secreted or shed into the medium by at least some tissue culture cells, and, in fact, is more readily detected by immunoprecipitation using spent medium than with solubilized cell extracts, thus serving as a basis for human cancer diagnosis in this system.

Both MF116 and MF61 show patterns of distribution which seem to be related to the embryological origin of the tissues. Thus, these antigens were detected on tumor cell lines of the ovary, uterus, kidney and bladder but not on cell lines from lung, colon, breast and pancreatic tumors. The former tumors are all from mesoderm-derived epithelia whereas the latter are endodermal or ectodermal in origin. The presence of the antigens in frozen sections of fresh tumor specimens of various types is currently being examined with the immunoperoxidase procedure. It is believed that MF116, MF61 and MH94, but not MD144, are expressed on a proportion of ovarian carcinomas.

The five antibodies described were selected from a large number of hybridoma antibodies produced to ovarian and endometrial cancer cell lines. Each mAb described is representative of a mAb class with similar characteristics. One problem in attempting to produce antibodies to restricted antigens of epithelial tumors is a tendency to produce many antibodies to common, strongly antigenic components. Another factor is that only a small fraction of ovarian carcinomas can be grown and maintained in tissue culture. This invention overcomes the problems. Removing strong antigens from a solubilized cell extract, by the use of immunoadsorbents, before immunization is also possible (Mattes, *Hybridoma* 2:523, 1983).

Diagnosis of cancer by the present invention comprises contacting a tissue containing ovarian and/or endometrial and/or cervical cells with the mAbs recognizing such cell antigens, preferably monoclonal antibodies to one or more cell antigens of the ovarian and/or endometrial and/or cervical antigenic system, and observing the immunoserological or immunopathological antigenic reaction between said monoclonal antibody and said antigen. In a preferred embodiment of the invention, the tissue sample or specimen or part thereof to be contacted is ovarian, cervical or endometrial tissue or cells or parts thereof and the antigenic reaction of the contacted tissue is observed by well known techniques such as immunofluorescence, ELISA, radioactive mAb, rosette formation with sheep or human red blood cells linked to Protein A or to anti-immunoglobulin, direct absorption and the like. In the case of shed antigens, body fluids and/or excretions or secretions can be tested in this manner.

In another preferred embodiment of the invention unknown human Cell specimens are analyzed for mAb reaction with each member of the cell panel using cell sorters for flow cytometry. Thus, the number of cells reacting with fluorescent mAb can be counted. The other well-known observation techniques can be employed to count the number of cells expressing the mAb antigen. In another embodiment of the present invention, the tissue to be assayed is first excised and is then either freshly, or after being frozen or embedded in paraffin by methods well-known in the art, contacted with the monoclonal antibodies of the invention. Observation of the reaction is as before.

In another preferred embodiment of the present invention, the tissue to be assayed comprises the intact body of an individual or whole portion thereof. The antibody, tagged with a radioactive or other energy-producing element, is administered to the individual, and the whole body or part thereof is scanned externally for localization of radioactivity at the site of cancerous cervical, endometrial or ovarian cells.

The present invention also makes possible the treatment of ovarian, cervical, or endometrial tumors in a patient wherein the monoclonal antibody recognizing the cell antigen of cancerous ovarian or endometrial cells, preferably the cell differentiation antigen, is administered to the patient in an amount effective to inhibit the growth or proliferation of cancer cells. In a preferred embodiment of this method, the antibody is tagged with a potentially tissue destructive agent which causes destruction of the cancer cells.

Examples of tissue destructive agents comprise chemotoxic agents, chemotherapeutic agents including vaccines, radionuclides, toxins, complement activators clotting activators and the like.

The invention also enables tissue typing using mAb-tissue immune reactions.

The above examples are for illustrative purposes only and are not meant to limit the scope of the invention.

The hybridoma cell lines producing the monoclonal antibodies of the same designation described above (MF116, MH94, MD144, MH55, MF61, ME46 and ME195) are on deposit and available at Memorial Sloan-Kettering Institute for Cancer Research, 1275 York Ave., New York, N.Y. 10021.

The hybridoma cell lines producing the monoclonal antibodies of the same designation as described above MF116, MH94, MD144, MH55 and MF61 have been deposited with the American Type Culture Collection (ATCC), 12301 Parklawn Drive, Rockville, Md. 20852 a recognized depository on Oct. 28, 1983 and have been given ATCC accession numbers of HB8409 for hybridoma cell line MD144 producing mAb MD144, HB8411 for hybridoma cell line MF116 producing mAb MF116, HB8412 for hybridoma cell line producing MH55 mAb MH55, HB8410 for hybridoma cell line MF61 producing mAb MF61 and HB8413 for hybridoma cell line MH94 producing mAb MH94.

The hybridoma cell lines producing the monoclonal antibodies of the same designation described above ME46 and ME195 have been deposited with the ATCC on Nov. 16, 1983 and have been given ATCC accession numbers of HB8431 for hybridoma cell line ME195 producing mAb ME195 and HB8430 for hybridoma cell line ME46 producing mAb ME46.

What is claimed:

1. Panel of monoclonal antibodies derived by immunization with an ovarian or a uterine cell line for the diagnosis of human uterine, cervical or ovarian cancer wherein the panel consists of at least two of the monoclonal antibodies selected from the group consisting of MF 116 (HB 8411), MH 94 (HB 8413), MD 144 (HB 8409), MH 55 (HB 8412), MF 61 (HB 8410), ME 46 (HB 8430) and ME 195 (HB 8431).

2. Method for diagnosis of malignant human ovarian, cervical or uterine cells which comprises contacting a human ovarian, cervical or uterine cell specimen, or shed antigen containing specimen thereof with one or more of the panel of monoclonal antibodies of claim 1 and immunologically detecting malignant ovarian, cervical, or uterine cells reacting with said monoclonal antibodies.

3. Monoclonal antibody panel of claim 1 wherein the immunogen cell lines are selected from the group consisting of ovarian cell lines SK-OV-3, SW 626, 2774 and uterine cell line SK-UT-1.

4. Hybridoma cell line producing any of the monoclonal antibodies of claim 1.

5. Panel of monoclonal antibodies for the diagnosis of human uterine, cervical or ovarian serous from mucinous cancer wherein the panel is selected from at least two of the group consisting of MF 116 (HB 8411), MH 94 (HB 8413), MD 144 (HB 8409), MH 55 (HB 8412), MF 61 (HB 8410), ME 46 (HB 8430) and ME 195 (HB 8431).

6. Kit for the diagnosis of ovarian, uterine or cervical cancer via shed or intact cell antigens comprisng in package form two or more of the monoclonal antibodies selected from the group consisting of MF 116 (HB 8411), MH 94 (HB 8413), MD 144 (HB 8409), MH 55 (HB 8412), MF 61 (HB 8410), ME 46 (HB 8430) and ME 195 (HB 8431).

* * * * *